US010314809B2

(12) United States Patent
Xing et al.

(10) Patent No.: US 10,314,809 B2
(45) Date of Patent: Jun. 11, 2019

(54) APPLICATION OF DERIVATIVE OF CLOSTRIDIUM GHONII

(71) Applicant: SHANDONG XINCHUANG BIOTECHNOLOGY CO., LTD., Jinan (CN)

(72) Inventors: Laitian Xing, Jinan (CN); Yong Wang, Jinan (CN); Mingqian Wei, Jinan (CN); Yanqiu Xing, Jinan (CN); Lianlian Li, Jinan (CN); Lichao Xing, Jinan (CN); Guangxia Deng, Jinan (CN); Hong Meng, Jinan (CN); Tao Huang, Jinan (CN); Dongxia Yang, Jinan (CN)

(73) Assignee: SHANDONG XINCHUANG BIOTECHNOLOGY CO., LTD., Jinan (CN)

(*) Notice: Subject to any disclaimer, the term of this patent is extended or adjusted under 35 U.S.C. 154(b) by 18 days.

(21) Appl. No.: 15/525,046

(22) PCT Filed: Jul. 8, 2015

(86) PCT No.: PCT/CN2015/083573
§ 371 (c)(1),
(2) Date: May 5, 2017

(87) PCT Pub. No.: WO2016/095503
PCT Pub. Date: Jun. 23, 2016

(65) Prior Publication Data
US 2017/0354633 A1  Dec. 14, 2017

(30) Foreign Application Priority Data

Dec. 19, 2014 (CN) .......................... 2014 1 0803072

(51) Int. Cl.
*A61K 31/337* (2006.01)
*A61K 35/742* (2015.01)
*A61K 9/19* (2006.01)
*A61P 35/00* (2006.01)

(52) U.S. Cl.
CPC .............. *A61K 31/337* (2013.01); *A61K 9/19* (2013.01); *A61K 35/742* (2013.01); *A61P 35/00* (2018.01)

(58) Field of Classification Search
None
See application file for complete search history.

(56) References Cited

U.S. PATENT DOCUMENTS 6,096,909 A * 8/2000 Ojima .................. C07D 305/14
549/510

FOREIGN PATENT DOCUMENTS

WO    WO 2013/159155    * 10/2013

* cited by examiner

*Primary Examiner* — Vera Afremova
(74) *Attorney, Agent, or Firm* — CBM Patent Consulting, LLC

(57) ABSTRACT

Application of Derivatives of *Clostridium ghonii*, especially in the application of Derivatives of *Clostridium ghonii* MW-DCG-HNCv-18 in preparation of medicines for treating non-small cell lung carcinoma. It also discloses a medicine combining the Derivatives of *Clostridium ghonii* MW-DCG-HNCv-18 strain with Docetaxel as the active ingredients. According to the invention, the MW-DCG-HNCv-18 strain is found to have specific inhibition effect on non-small cell lung carcinoma for the first time, the inhibition effect on the non-small cell lung carcinoma is significantly superior to that of other known similar strains, and through screening, the MW-DCG-HNCv-18 strain is found to have more prominent inhibition effect on non-small cell lung carcinoma when combined with Docetaxel injection.

5 Claims, 2 Drawing Sheets

APPLICATION OF DERIVATIVE OF CLOSTRIDIUM GHONII

This application is the U.S. national phase of International Application No. number PCT/CN2015/083573 filed on 8 Jul. 2015 which designated the U.S. and claims priority to Chinese Application Nos. filed CN 201410803072.X filed on 19 Dec. 2014, the entire contents of each of which are hereby incorporated by reference.

TECHNICAL FIELD

The invention relates to application of Derivatives of *Clostridium ghonii* (DCG), and in particular relates to application of DCG in preparation of medicines for treating non-small cell lung carcinoma (NSCLC), belonging to the technical field of biomedicines.

BACKGROUND TECHNOLOGY

At present, the understanding of pathophysiology of solid tumors is increasingly turning to their unique growth microenvironments. The center areas of the solid tumors are characterized by increased interstitial pressure, lowered cell pH, low oxygen content and tumor cell heterogeneity. The tumor microenvironments are also an important reason for tumor metastasis, invasion and insensitivity to conventional radiotherapy and chemotherapy. First, the solid tumors contain hypoxic or necrotic areas, the hypoxic areas are far away from the blood vessels and are not rich in blood supply, and high interstitial pressure exists in the tumor centers, so that the tumor cells in the hypoxic areas difficulty obtain effective medicine concentration, and thus the hypoxic areas cannot be effectively treated by the conventional chemotherapy. Second, radiotherapy relies on the formation of oxygen free radicals, resulting in DNA damage in mitotic cells, so the lack of the oxygen free radicals in the tumor centers reduces the DNA damage during processing. Third, most chemotherapeutic medicines are effective only for rapid dividing tumor cells, and have poor efficacy in hypoxic tumor cells, stromal cells, and tumor tissue structures that have ceased to divide (fibronectin and collagen). Moreover, the conventional radiotherapy and chemotherapy often lack specific effects on tumor cells. The tumor anaerobic microenvironments limit the efficacy of the conventional radiotherapy and chemotherapy as well as viral therapy, but provide a good opportunity for anaerobic bacteria to grow and play oncolysis effects in the hypoxic areas of the tumors.

DCG is obligate anaerobe Gram-positive bacillus, which has two growth states: spore and vegetative states. DCG spores are very weak in antigen property, and can be used as a preparation for intravenous injection to reduce the organism stimulation. Due to disordered vascular tissue structures of the tumors, the DCG spores in the blood can easily enter the tumor tissues, and germinate, reproduce, and secret lipase, protease and other hydrolases in the tumor hypoxic/necrotic areas to effectively and indiscriminately destroy various cells (tumor cells, non-cancerous interstitial cells, active dividing cells, stem cells or resting cells, etc.) and tumor structures (fibronectin and collagen) in the tumor tissue, causing oncolytic necrosis of the most of the tumors and achieving all the parenchyma and interstitial digestion of the tumors. The tumor microenvironments are destroyed and altered fundamentally. The destroying of the tumor microenvironments effectively restrains or reverses the tumor growth and destroys the tumor-forming condition, and even leads to the almost complete destroying and disappearance of the whole tumors, thereby being possible for NSCLC deep processing. The hydrolases secreted by DCG dissolve tumor tissue-induced inflammatory response and directly involve in the destroying of reactive oxygen species, protease and other degrading enzymes on the tumor cells. More importantly, the inflammatory response can stimulate the organism to produce a strong cellular immune response, and destroy the residual tumor cell microenvironments.

Chinese Patent CN103374538A (Application No. 201210310374.4) discloses a derivative bacterial strain of avirulent and non-pathogenic *Clostridium ghonii*, which is capable of inhibiting the growth of one or more solid tumors, and reversing or destroying one or more solid tumors. CN103374538A also relates to a composition of derivative bacterial strain, targeting the dissolution of the solid tumors.

However, due to the different formation reasons of the solid tumors, the effects of different strains on the solid tumors are specific. Therefore, further study on the specific effects of different strains on different solid tumors has become a hotspot in this field.

SUMMARY OF THE INVENTION

Aiming at the shortcomings of the existing technology, the invention provides application of a Derivatives of *Clostridium ghonii* MW-DCG-HNCv-18 strain, especially in the application of the preparation of medicines for treating non-small cell lung carcinoma.

The Derivatives of *Clostridium ghonii* MW-DCG-HNCv-18 strain has white colonies on a reinforced clostridial-agar medium, is rounded, about 1-2 mm in diameter and slightly sticky, and has rough edges and consistent sizes. The vegetative mass is singly growing short stem straight cells, and the thalli are 0.3-1.5 μm in width and 8-16 μm in length, and are Gram-positive. The spores are located near the end of the thalli and are oval. The strain is known and is available from the National Measurement Institute (Australia), with strain collection number of V12/001485.

A medicine for treating non-small cell lung carcinoma comprises a pharmaceutical composition prepared from the Derivatives of *Clostridium ghonii* MW-DCG-HNCv-18 strain and Docetaxel as active ingredients as well as pharmaceutically acceptable excipients.

According to a preferred embodiment of the invention, the ratio of the Derivatives of *Clostridium ghonii* MW-DCG-HNCv-18 strain spores to Docetaxel is that per mg of Docetaxel is combined with $5 \times 10^6$-$3.0 \times 10^7$ strain spores.

According to a further preferred embodiment of the invention, the ratio of the Derivatives of *Clostridium ghonii* MW-DCG-HNCv-18 strain spores to Docetaxel is that per mg of Docetaxel is combined with $1.0 \times 10^7$-$2.0 \times 10^7$ strain spores.

According to a more preferred embodiment of the invention, the ratio of the Derivatives of *Clostridium ghonii* MW-DCG-HNCv-18 strain spores to Docetaxel is that per mg of Docetaxel is combined with $1.5 \times 10^7$ strain spores.

According to a preferred embodiment of the invention, the dosage form of the medicine for treating non-small cell lung carcinoma is spore freeze-dried powder for injection.

The spore freeze-dried powder for injection can be prepared by a low-temperature freeze-drying technology.

According to a further preferred embodiment of the invention, the spore freeze-dried powder for injection is mixed with a solvent for use, wherein the solvent is selected from Ringer's solution, saline with mass concentration of 0.9%, and phosphate buffer. The solvent is required to meet the requirements of nontoxicity and injectability. The medicine is administrated through intravenous, spinal, intramuscular, subcutaneous, intratumoral injection and intraperitoneal manners.

Beneficial Effects

1. The MW-DCG-HNCv-18 strain is found to have specific inhibition effect on non-small cell lung carcinoma for the first time in the invention, the inhibition effect on the non-small cell lung carcinoma is significantly superior to that of other known similar strains, and through screening, the MW-DCG-HNCv-18 strain is found to have more prominent inhibition effect on non-small cell lung carcinoma when combined with Docetaxel injection, so that a novel way is provided for the treatment of non-small cell lung carcinoma.
2. The DCG spores of the invention have the characteristic of obligate anaerobic, and can move to the hypoxic areas of the tumors, causing oncolytic necrosis of the most of the tumors, when they reach the edges of oxygen-rich tumors, bacterial proliferation and movement stagnate, the residual tumor tissues at the edges still have potential for recurrence, and Docetaxel can kill the rapid dividing tumor cells in the oxygen-rich environment at the edges of the tumor tissues at lower doses. At the same time, chemotherapy medicines can also increase the degree of hypoxia in the tumors by destroying the blood vessels of the tumors, thereby being more conducive to DCG colonization and improving oncolytic effect. The DCG spores and the chemotherapy medicines synergistically form a tumor-targeting three-dimensional and highly-targeted oncolytic effect to achieve complementary advantages, both inside and outside attack, and "super-superposition effect".

DRAWING DESCRIPTION

EMBODIMENTS

Figure 1:
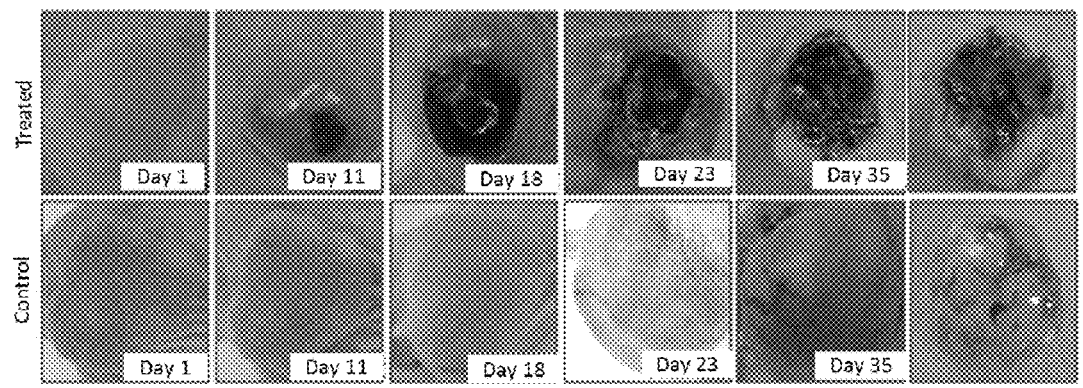
FIG. 1 is a picture of the anti-tumor effect of MW-DCG-HNCv-18 in Example 1.

The invention will be further described with reference to the following examples, but the scope of the invention is not limited thereto.

Source of Strain

The MW-DCG-HNCv-18 strain is from the National Measurement Institute (Australia), with strain collection number of V12/001485.

The MW-DCG-LCv-26 strain is from the National Measurement Institute (Australia), with strain collection number of V12/001486.

The MW-DCG-CCv-17 strain is from the National Measurement Institute (Australia), with strain collection number of V12/001487.

The *Clostridium novyi*-NT strain is from ATCC, with strain collection number of ATCC®7659™.

Cetuximab (5 mg/ml) is purchased from Germany MERCK Serono, with production lot number: 132393, and production date: February 2013.

Docetaxel is purchased from Qilu Pharmaceutical Co., Ltd., with production lot number: 3030062TA, and production date: Mar. 18, 2013.

Adriacin is purchased from Shenzhen Wanle Pharmaceutical Co., Ltd., with production lot number|: 1206E4, and production date: April 2013.

Example 1

Study Method:

☐Construction of Non-Small Cell Lung Carcinoma Models

The non-small cell lung carcinoma A549 cells were injected into the subcutaneous positions at femoral lateral parts of right backs of female Balb/c-nu/nu nude mice (5 weeks old, 20 g) by subcutaneous injection. The in-vivo anti-tumor test was performed when the tumor volume was 300 mm$^3$.

② Animal Grouping and Processing

Control group: n=15 (n is the number of animals in each group), and 0.2 ml of PBS buffer was intravenously injected to the tails;

MW-DCG-HNCv-18 spore group: n=15, spores were intravenously injected to the tails on the first day, and the dose was $3\times10^8$/(kg·body weight).

MW-DCG-LCv-26 spore group: n=15, spores were intravenously injected to the tails on the first day, and the dose was $3\times10^8$/(kg·body weight).

MW-DCG-CCv-17 spore group: n=15, spores were intravenously injected to the tails on the first day, and the dose was $3\times10^8$/(kg·body weight).

*C. novyi*-NT spore group: n=15, spores were intravenously injected to the tails on the first day, and the dose was $3\times10^8$/(kg·body weight).

③ Detection Index

The major diameter (a) and transverse diameter (b) of the transplanted tumors of the nude mice were measured with a vernier caliper, 3 to 4 times a week. At the same time, the general situations of tumor-bearing mice, including body weight, feeding, drinking, mental state, behavior, fur color, excretion and death were observed and recorded.

④ Evaluation Standard

The tumor volume ($V=\frac{1}{2}\times a \times b^2$) was calculated according to the measured major diameter and transverse diameter data of the tumors, the curve was drawn and the tumors were observed dynamically.

Tumor inhibition rate (%)=(average tumor weight in the control group−average tumor weight in the test group)/average tumor weight in the control group×100%.

Tumor necrosis rate (%)=cross-sectional area of the necrotic area/cross-sectional area of the entire tumor×100%.

Tumor oncolysis rate (%)=number of animals undergoing tumor oncolysis/total number of animals in this group×100%.

The overall survival time of tumor-bearing mice: the nude mice in each group after processing were fed until natural death, and the survival time was calculated.

⑤ Result

| Group | Tumor inhibition rate | Necrosis rate | Oncolysis rate | Mean survival days | Toxicity level |
|---|---|---|---|---|---|
| Control group | 0 | 0 | 0 | 25.0 day | No |
| MW-DCG-HNCv-18 group | 51.1% | 76.55% | 100% | 45.8 day | No |
| MW-DCG-LCv-26 group | 39.3% | 65.00% | 68% | 36.3 day | No |
| MW-DCG-CCv-17 group | 36.9% | 59.27% | 68% | 34.5 day | No |
| C. novyi-NT group | 47.8% | 71.42% | 84% | 32.0 day | Yes (body weight decrease) |

Consequently, (1) Effectiveness: compared with the MW-DCG-LCv-26 strain and MW-DCG-CCv-17 strain, the MW-DCG-HNCv-18 has tumor inhibition rate, necrosis rate and oncolysis rate to the NSCLC tumor-bearing mice model of 51.1%, 76.55% and 100%, respectively, which are significantly higher than those of the MW-DCG-LCv-26 strain and MW-DCG-CCv-17 strain. Compared with the C. novyi-NT strain, the MW-DCG-HNCv-18 strain has higher tumor inhibition rate, necrosis rate and oncolysis rate, but the difference was not significant. At the same time, the study results show that there is a large area of necrosis after the 35th day of spore injection in the MW-DCG-HNCv-18 spore group, while the tumor volume in the control group is continued to increase (FIG. 1).

(2) Safety: the MW-DCG-HNCv-18 strain prolongs the mean survival days of the tumor-bearing mice compared with the MW-DCG-LCv-26, MW-DCG-CCv-17 and C. novyi-NT strains, and the mean survival days are significantly longer than those of the tumor-bearing mice in the C. novyi-NT group. The studies find that the body weight of the tumor-bearing mice in the C. novyi-NT group decreases, while the body weight of the tumor-bearing mice in the other three groups does not change.

It is found that the MW-DCG-HNCv-18 strain shows good effectiveness and safety compared with the MW-DCG-LCv-26, MW-DCG-CCv-17 and C. novyi-NT strains.

Example 2

Study Method:
① Construction of Non-Small Cell Lung Carcinoma Models

The non-small cell lung carcinoma A549 cells were injected into the subcutaneous positions at femoral lateral parts of right backs of female Balb/c-nu/nu nude mice (5 weeks old, 20 g) by subcutaneous injection. The in-vivo test was performed when the tumor volume was 300 mm$^3$.

② Animal Grouping and Processing

Control group: n=15, and 0.2 ml of PBS buffer was intravenously injected to the tails;

Docetaxel group: n=15, Docetaxel was intravenously injected to the tails on the 4th day and 11th day, the dose was 20 mg/(kg·body weight), and the application dose of Docetaxel was the optimal application dose.

MW-DCG-HNCv-18 spore group: n=15, spores were intravenously injected to the tails, and the dose was $3 \times 10^8$/(kg·body weight).

MW-DCG-HNCv-18 spore+Cetuximab group: n=15, MW-DCG-HNCv-18 spores were intravenously injected to the tails on the first day, and the dose was $3 \times 10^8$/(kg·body weight); Cetuximab was intravenously injected to the tails on the 4th day and 11th day, the dose was 70 mg/(kg·body weight), and the application dose of Cetuximab was the optimal application dose.

MW-DCG-HNCv-18 spore+Cetuximab group: n=15, MW-DCG-HNCv-18 spores were intravenously injected to the tails on the first day, and the dose was $3 \times 10^8$/(kg·body weight); Adriacin was intravenously injected to the tails on the 4th day and 11th day, the dose was 10 mg/(kg·body weight), and the application dose of Adriacin was the optimal application dose.

MW-DCG-HNCv-18 spore+Docetaxel group: n=15, MW-DCG-HNCv-18 spores were intravenously injected to the tails on the first day, and the dose was $3 \times 10^8$/(kg·body weight); Docetaxel was intravenously injected to the tails on the 4th day and 11th day, and the dose was 20 mg/(kg·body weight).

C. novyi-NT spore+Docetaxel group: n=15, C. novyi-NT spores were intravenously injected to the tails on the first day, and the dose was $3 \times 10^8$/(kg·body weight);

Docetaxel was intravenously injected to the tails on the 4th day and 11th day, and the dose was 20 mg/(kg·body weight).

③ Detection Index

The major diameter (a) and transverse diameter (b) of the transplanted tumors of the nude mice were measured with a vernier caliper, 3 to 4 times a week, the tumor volume of each group was calculated, and the anti-tumor effects of the strains were observed dynamically. At the same time, the body weight, feeding, drinking, mental state, behavior, fur color, excretion and death situations of the tumor-bearing mice were observed and recorded.

④ Evaluation Standard

The tumor volume ($V=\frac{1}{2} \times a \times b^2$) was calculated according to the measured major diameter and transverse diameter data of the tumors, the curve was drawn and the tumors were observed dynamically.

Tumor inhibition rate (%)=(average tumor weight in the control group−average tumor weight in the test group)/average tumor weight in the control group×100%.

Tumor necrosis rate (%)=area of the necrotic area/area of the entire tumor×100%.

Cure rate (%)=number of animals with tumor completely removed/total number of animals in this group×100%.

The overall survival time of the tumor-bearing mice: the nude mice in each group after processing were fed until natural death, and the survival time was calculated.

⌐Result

| Group | Tumor inhibition rate | Necrosis rate | Cure rate | mean survival days |
|---|---|---|---|---|
| Control group | 0 | 0 | 0% | 24.4 day |
| Docetaxel group | 55.9% | 22.2 | 0% | 35.5 day |
| MW-DCG-HNCv-18 group | 51.4% | 76.6 | 0% | 43.8 day |
| MW-DCG-HNCv-18 + Cetuximab group | 59.9% | 76.1% | 13.3% | 58.2 day |
| MW-DCG-HNCv-18 + Adriacin group | 57.7% | 74.7% | 0% | 47.0 day |
| MW-DCG-HNCv-18 + Docetaxel group | 79.8% | 91.2% | 26.7% | 71.0 day |
| C. novyi-NT + Docetaxel group | 67.4% | 78.6% | 13.3% | 53.6 day |

Figure 2:
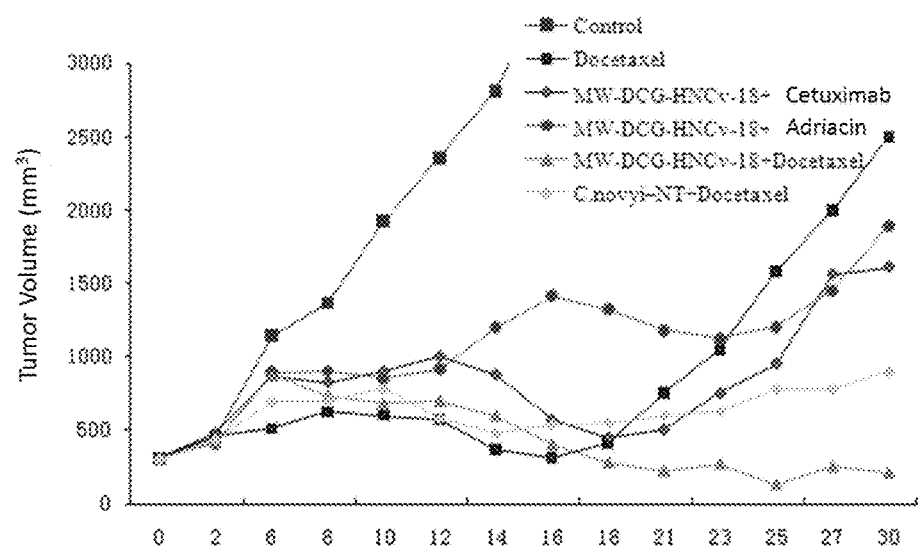
FIG. 2 is tumor growth curves of various test groups obtained by testing in Example 2.
Figure 3:
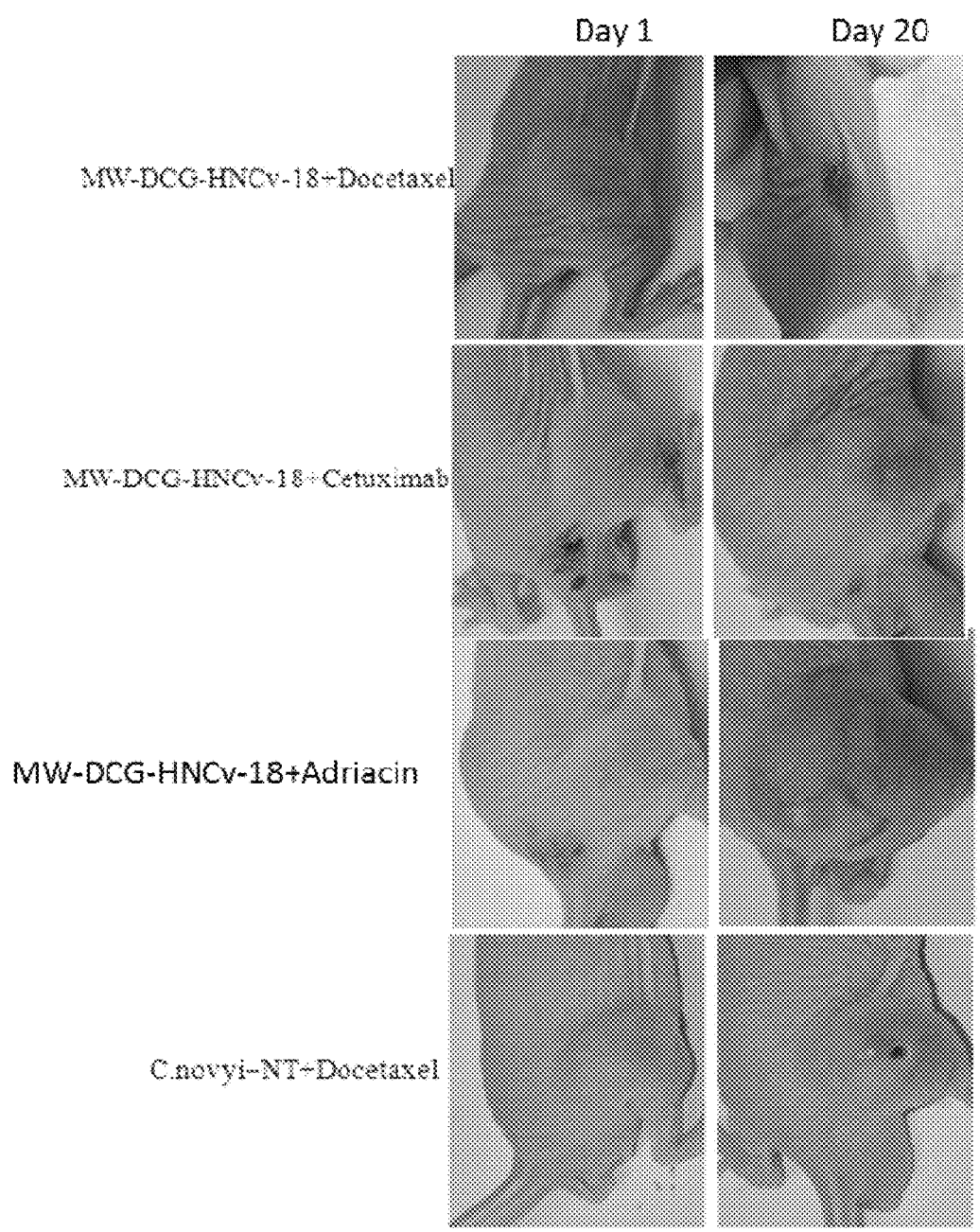
FIG. 3 is a result picture of the anti-tumor effect at 20th day in testing in Example 2.

Consequently, the MW-DCG-HNCv-18+Docetaxel group has significantly higher tumor inhibition rate and necrosis rate to the non-small cell lung carcinoma tumor-bearing mice model than other combined administration groups. The tumor volumes of the tumor-bearing mice in the MW-DCG-HNCv-18+Docetaxel group are inhibited from the 6th day after administration, and are always kept at about 300 mm$^3$, while the tumor volumes of the tumor-bearing mice in the other groups increase to different extents (FIG. 2). At the same time, the tumors of 26.7% of the tumor-bearing mice in the MW-DCG-HNCv-18+Docetaxel group are almost completely removed (FIG. 1), regarding as cure, and the cure rate is significantly higher than that of the other three combined administration groups.

The MW-DCG-HNCv-18+Docetaxel group prolongs the survival days of the tumor-bearing mice to 71.0 days, which are 2.9 times those of the tumor-bearing mice in the control group, and are significantly longer than those of the MW-DCG-HNCv-18+Cetuximab group, the MW-DCG-HNCv-18+Adriacin group and the C. novyi-NT+Docetaxel group. It is found that the MW-DCG-HNCv-18 in combination Docetaxel for treatment of the non-small cell lung carcinoma shows super-superposition effects.

Example 3

Study Method:
① Construction of Non-Small Cell Lung Carcinoma Models

The non-small cell lung carcinoma A549 cells were injected into the subcutaneous positions at femoral lateral parts of right backs of female Balb/c-nu/nu nude mice (5 weeks old, 20 g) by subcutaneous injection. The in-vivo test was performed when the tumor volume was 300 mm$^3$.
② Animal Grouping and Processing Control group: n=15, and 0.2 ml of PBS buffer was intravenously injected to the tails;

MW-DCG-HNCv-18 spore+Docetaxel-1 group: n=15, MW-DCG-HNCv-18 spores were intravenously injected to the tails on the first day, and the dose was 0.5×10$^8$/(kg·body weight); Docetaxel was intravenously injected to the tails on the 4th day and 11th day, and the dose was 20 mg/(kg·body weight).

MW-DCG-HNCv-18 spore+Docetaxel-2 group: n=15, MW-DCG-HNCv-18 spores were intravenously injected to the tails on the first day, and the dose was 1.0×10$^8$/(kg·body weight); Docetaxel was intravenously injected to the tails on the 4th day and 11th day, and the dose was 20 mg/(kg·body weight).

MW-DCG-HNCv-18 spore+Docetaxel-3 group: n=15, MW-DCG-HNCv-18 spores were intravenously injected to the tails on the first day, and the dose was 2.0×10$^8$/(kg·body weight); Docetaxel was intravenously injected to the tails on the 4th day and 11th day, and the dose was 20 mg/(kg·body weight).

MW-DCG-HNCv-18 spore+Docetaxel-4 group: n=15, MW-DCG-HNCv-18 spores were intravenously injected to the tails on the first day, and the dose was 3.0×10$^8$/(kg·body weight); Docetaxel was intravenously injected to the tails on the 4th day and 11th day, and the dose was 20 mg/(kg·body weight).

MW-DCG-HNCv-18 spore+Docetaxel-5 group: n=15, MW-DCG-HNCv-18 spores were intravenously injected to the tails on the first day, and the dose was 5.0×10$^8$/(kg·body weight); Docetaxel was intravenously injected to the tails on the 4th day and 11th day, and the dose was 20 mg/(kg·body weight).

MW-DCG-HNCv-18 spore+Docetaxel-6 group: n=15, MW-DCG-HNCv-18 spores were intravenously injected to the tails on the first day, and the dose was 6.0×10$^8$/(kg·body weight); Docetaxel was intravenously injected to the tails on the 4th day and 11th day, and the dose was 20 mg/(kg·body weight).

MW-DCG-HNCv-18 spore+Docetaxel-7 group: n=15, MW-DCG-HNCv-18 spores were intravenously injected to the tails on the first day, and the dose was 7.0×10$^8$/(kg·body weight); Docetaxel was intravenously injected to the tails on the 4th day and 11th day, and the dose was 20 mg/(kg·body weight).
③ Detection Index The major diameter (a) and transverse diameter (b) of the transplanted tumors of the nude mice were measured with a vernier caliper, 3 to 4 times a week. At the same time, the body weight, feeding, drinking, mental state, behavior, fur color, excretion and death situations of the tumor-bearing mice were observed and recorded.
④ Evaluation Standard The tumor volume (V=½×a×b$^2$) was calculated according to the measured major diameter and transverse diameter data of the tumors, the curve was drawn and the tumors were observed dynamically.

Tumor inhibition rate (%)=(average tumor weight in the control group−average tumor weight in the test group)/average tumor weight in the control group×100%.

Tumor necrosis rate (%)=cross-sectional area of the necrotic area/cross-sectional area of the entire tumor×100%.

Cure rate (%)=number of animals with tumor completely removed/total number of animals in this group×100%.

The overall survival time of the tumor-bearing mice: the nude mice in each group after processing were fed until natural death, and the survival time was calculated.

☐Result

| Group | Tumor inhibition rate | Necrosis rate | Cure rate | mean survival days |
|---|---|---|---|---|
| Control group | 0 | 0 | 0 | 26.8 day |
| MW-DCG-HNCv-18 spore + Docetaxel-1 group | 52.4% | 44.4% | 0% | 41.2 day |
| MW-DCG-HNCv-18 spore + Docetaxel-2 group | 64.2% | 76.1% | 0% | 49.0 day |
| MW-DCG-HNCv-18 spore + Docetaxel-3 group | 68.9% | 80.2% | 13.3% | 56.0 day |
| MW-DCG-HNCv-18 spore + Docetaxel-4 group | 79.7% | 90.7% | 26.7% | 71.3 day |
| MW-DCG-HNCv-18 spore + Docetaxel-5 group | 79.4% | 84.6% | 13.3% | 66.4 day |
| MW-DCG-HNCv-18 spore + Docetaxel-6 group | 79.1% | 85.5% | 13.3% | 66.0 day |
| MW-DCG-HNCv-18 spore + Docetaxel-7 group | 79.5% | 87.9% | 0% | 54.7 day |

According to the above results, the tumor inhibition rate, necrosis rate, cure rate and mean survival days of the MW-DCG-HNCv-18 spore+Docetaxel-1 group are significantly lower than those of other MW-DCG-HNCv-18 spore+Docetaxel groups.

In the MW-DCG-HNCv-18 spore+Docetaxel-2 group, MW-DCG-HNCv-18 spore+Docetaxel-3 group and MW-DCG-HNCv-18 spores+Docetaxel-4 group, with the increase of MW-DCG-HNCv-18 spore dose, the tumor inhibition rate, necrosis rate, cure rate and mean survival days gradually increase, and the anti-tumor effect of the MW-DCG-HNCv-18 spore+Docetaxel-4 group is the best.

Compared with the MW-DCG-HNCv-18 spore+Docetaxel-4 group, the MW-DCG-HNCv-18 spore+Docetaxel-7 group is not significantly different in the tumor inhibition rate and necrosis rate, but significantly lower in the cure rate and mean survival days.

Considering the production cost of the MW-DCG-HNCv-18 spores, it is considered that the preferred range of the MW-DCG-HNCv-18 spores in combination with Docetaxel for the treatment of non-small cell lung carcinoma should be $1.0 \times 10^8$-$6.0 \times 10^8$/(kg·body weight), and the most preferred dose is $3.0 \times 10^8$ cells/(kg·body weight).

What is claimed is:

1. A pharmaceutical composition for treating non-small cell lung carcinoma, wherein the pharmaceutical composition includes *Clostridium ghonii* MW-DCG-HNCv-18 deposited at the National Measurement Institute (NMI) under NMI accession number V12/001485, Docetaxel, and pharmaceutically acceptable excipients; the ratio of spores of *Clostridium ghonii* MW-DCG-HNCv-18 to the Docetaxel is $5 \times 10^6$-$3.0 \times 10^7$:1 mg.

2. The pharmaceutical composition according to claim 1, wherein the ratio of the spores of *Clostridium ghonii* MW-DCG-HNCv-18 to the Docetaxel is $1.0 \times 10^7$-$2.0 \times 10^7$:1 mg.

3. The pharmaceutical composition according to claim 2, wherein the ratio of the spores of *Clostridium ghonii* MW-DCG-HNCv-18 to the Docetaxel is $1.5 \times 10^7$:1 mg.

4. The pharmaceutical composition according to claim 1, wherein the spores are in a form of a spore freeze-dried powder for injection.

5. The pharmaceutical composition according to claim 4, wherein the spore freeze-dried powder for injection is mixed with a solvent for use, wherein the solvent is selected from a group consisting of Ringer's solution, saline with mass concentration of 0.9%, and phosphate buffer.

* * * * *